United States Patent [19]

Walles et al.

[11] Patent Number: 4,533,484

[45] Date of Patent: Aug. 6, 1985

[54] PIGMENTS FOR TOILETRIES

[75] Inventors: Wilhelm E. Walles, Freeland; William H. Keskey; Richard G. Young, both of Midland, all of Mich.

[73] Assignee: The Dow Chemical Company, Midland, Mich.

[21] Appl. No.: 539,496

[22] Filed: Oct. 6, 1983

[51] Int. Cl.$^3$ .......................... C08J 3/20; C09B 69/10; C09F 26/06; C11D 9/20

[52] U.S. Cl. ........................................ 252/117; 8/524; 8/525; 8/552; 8/572; 8/637; 8/647; 252/134; 252/DIG. 16; 424/49; 424/78; 526/260

[58] Field of Search .................. 8/524, 525, 526, 553, 8/572, 552, 637, 647; 526/260, 264; 252/117, 134, DIG. 16; 424/49, 78

[56] References Cited

U.S. PATENT DOCUMENTS

| | | | |
|---|---|---|---|
| 2,265,127 | 12/1941 | Bolton | 8/516 |
| 2,919,279 | 12/1959 | Walles | 524/903 |
| 2,946,772 | 7/1960 | Walles | 260/77.5 |
| 2,946,773 | 7/1960 | Walles | 260/77.5 |
| 2,948,708 | 8/1960 | Walles | 526/264 |
| 3,030,339 | 4/1962 | Tousignant | 8/102 |
| 3,051,676 | 8/1962 | Bakke | 524/158 |
| 3,097,046 | 7/1963 | Walles | 8/554 |
| 3,097,048 | 7/1963 | Walles | 8/102 |
| 3,108,992 | 10/1963 | Moore | 260/88.1 |
| 3,241,905 | 3/1966 | Olaj | 8/553 |
| 3,249,393 | 5/1966 | Haas | 8/4 |
| 3,284,414 | 11/1966 | Lashua | 526/260 |
| 3,328,357 | 6/1967 | Lashua | 526/260 |
| 3,355,518 | 11/1967 | Sullivan | 526/260 |
| 3,412,036 | 11/1968 | McIntosh | 8/647 |
| 3,539,540 | 11/1970 | Walles | 260/80.3 |
| 3,832,431 | 8/1974 | Matthaei | 252/134 |
| 4,083,689 | 4/1978 | Wolf | 8/85 B |
| 4,113,674 | 9/1978 | Miller | 8/31 |
| 4,245,992 | 1/1981 | Yamashita | 8/461 |
| 4,336,244 | 6/1982 | Woznicki | 424/35 |
| 4,405,757 | 9/1983 | Howell | 525/326.9 |

OTHER PUBLICATIONS

"New Dow Polymers Complex Many Organics", Article in C & E News, Sep. 5, 1960, pp. 56 & 57.
Derwent Abstract 30858B/16 of Japanese Kokai, 100287, (1979), published 3/12/79.

Primary Examiner—Dennis L. Albrecht

[57] ABSTRACT

Methods of rendering water-soluble dyes insoluble comprise contacting a polymer containing X-alkyl-2-oxazolidinone with the desired dye or dyes. The essentially water-insoluble pigments so prepared are useful in a wide variety of uses and, in particular, in coloring soaps, toothpaste, etc.

20 Claims, No Drawings

PIGMENTS FOR TOILETRIES

BACKGROUND OF THE INVENTION

The present invention relates to methods for preparing pigments and to methods for using said pigments.

It is often desirable to provide household toiletries such as soap bars and toothpaste with pleasant colors. Such colors are provided to said toiletries through the use of dyes and pigments. For example, green pigment has been introduced to soap and toothpaste through the addition of chlorophyll to said products. Unfortunately, such a pigment is high in price and is difficult to color match, thus resulting in quality control problems.

It has also been common practice to introduce organic and/or inorganic pigments to soap or toothpaste. For example, green pigment can be introduced to said products via the use of phthalocyanine pigments or via the addition of chromium hydroxide. Although such inorganic pigments are relatively cheap to produce and are fairly simple to color match, such pigments pose potential toxicity problems and/or introduce heavy metals into municipal sewage systems.

In order to avoid the potential toxicity problems introduced to toiletries via the addition or organic and/or inorganic pigments thereto, it would be highly desirable to use government approved food, drug and cosmetic dyes into said toiletries. Unfortunately, such dyes are typically water-soluble and introduce disadvantages when used in coloring soaps and toothpaste. For example, water-soluble dyes will leave an undesirable color on skin, towels, etc. and will often complex with proteinous materials such as skin. In addition, as soap bars are wetted and rewetted, water-soluble dyes will tend to run and consequently stain sinks, bathtubs, etc.

In view of the deficiencies of the prior art, it would be highly desirable to provide a method of coloring toiletries using nontoxic, water-soluble dyes, wherein such dyes are introduced to said toiletries in a water-insoluble, pigment form.

SUMMARY OF THE INVENTION

In one aspect, the present invention is a method for preparing a substantially water-insoluble organic pigment wherein a water-soluble dye is contacted with a polymer comprising X-alkyl-2-oxazolidinone moieties to yield pigment particles having the insolubility characteristics of the polymer and the color characteristics of the dye. The polymer is insoluble in an aqueous medium at temperatures in the typical range in which the resulting pigment is used and the pigments so prepared do not bleed when contacted with an aqueous medium. In another aspect, the present invention is a pigment which is prepared via the aforementioned process.

In another aspect, the present invention is a method for introducing water-soluble, organic dyes to toiletries such that the dyes added thereto are rendered substantially water-insoluble through the preparation of a polymer-dye pigment.

DETAILED DESCRIPTION OF THE INVENTION

As used herein, the term "pigment" is meant to include any substance, usually in finely divided (i.e., powder) form, that is highly colored and imparts color to another substance or mixture as a result of dispersion therein. A pigment is generally insoluble in an aqueous medium under normal conditions of use.

As used herein, the term "dye" is meant to include an organic species which is essentially water-soluble in an aqueous medium and which can become chemically bound to the material to which it is applied. Although almost any dye which will complex with copolymers used herein can be employed, preferred dyes which are most desirable are those salts which are designated by the United States Food and Drug Administration as Food, Drug and Cosmetic (FD&C) colors. For example, FD&C Blue No. 1, Blue No. 2, Green No. 3, Green No. 6, Red No. 3, Yellow No. 5, Yellow No. 6, Yellow No. 7, and Yellow No. 10 are especially preferred dyes.

Polymers useful herein are those well-known poly-N-vinyl-X-alkyl-2-oxazolidinones which are insoluble in an aqueous medium under conditions in which the toiletries are employed. Examples of such polymers and methods of their preparation are disclosed in U.S. Pat. No. 3,539,540 which is incorporated herein by reference. Also preferred are those copolymers which have cloud points in the temperature range and under conditions which the toiletries are employed. Suitable copolymers are disclosed in U.S. Pat. Nos. 2,946,772 and 2,946,773 which are incorporated herein by reference. Of the foregoing polymers, those prepared from the polymerization of N-vinyl-5-methyl-2-oxazolidinone or N-vinyl-5-ethyl-2-oxazolidinone are most preferred.

One method of preparing pigments comprises contacting the aforementioned polymer with an aqueous medium under conditions in which the polymer is at least partially soluble. Typically, said polymers are contacted with cold water. To this solution or dispersion is added a slight excess of the desired dye or combination of dyes. The temperature of the solution or dispersion is then raised and a highly colored precipitate results which can be filtered and dried. Typically, the use of poly-N-vinyl-5-ethyl-2-oxazolidinone and a dye will yield a pigment which is insoluble in an aqueous liquid (i.e., a true pigment) at temperatures above about 3° C.

Another method for preparing pigments comprises first preparing a resin bead comprising polystyrene slightly crosslinked with divinylbenzene wherein the aromatic ring is chloromethylated in the para position. The resulting —$CH_2Cl$ is then reacted with the desired X-alkyl-2-oxazolidinone moiety resulting in the desired polyvinyl benzyl X-alkyl-2-oxazolidinone. See, for example, U.S. Pat. No. 3,108,992. The beads so prepared are placed into an aqueous solution containing the desired dye or dyes. The mixture is stirred, preferably at room temperature, for a period of time ranging from about 1 minute to one hour. The beads can be filtered, washed with water and dried.

Another method for preparing pigments comprises introducing the desired dye or dyes to the reaction medium containing the N-vinyl-X-alkyl-2-oxazolidinone monomer. The monomer is polymerized using known techniques to yield a water-insoluble polymer-dye pigment.

A less preferred method of preparing pigments comprises contacting a copolymer of a hydrophobic monomer and an N-vinyl-X-alkyl-2-oxazolidinone with an aqueous medium under conditions which the polymer is at least partially soluble. This is accomplished by employing a monomer which comprises sufficient hydrophobic character such that the resulting copolymer is essentially insoluble in the aqueous liquid at temperatures which the resulting pigment is employed. Examples of such monomers include styrene, vinyl toluene, vinyl acetate, and the like. The desired dye is added to the solution or dispersion of copolymer. The slurry of essentially insoluble copolymer and dye form a pigment which can be filtered and dried. The complex formed between the aforementioned copolymer and dye will yield a pigment which is insoluble in an aqueous liquid (i.e., a true pigment) at temperatures in the range from about 3° C. to about 39° C., depending upon the copolymer.

The size of the precipitated pigment particles can vary and is not particularly critical. Preferably, the particle ranges from about 1 $\mu$m to about 5 $\mu$m in diameter. The size of the particle can be controlled through techniques such as controlled temperature rise and controlled stirring speed during precipitation steps. It is also understood that large size particles can be ground to the desired size.

The pigments prepared via the process of this invention are highly stable to degradation under conditions of normal use. Thus, when contacted with aqueous liquids, the pigments do not exhibit bleeding. The pigments are highly stable over a wide pH range even in aqueous media containing surfactants.

The particulate pigments are added to toiletries as soaps (e.g. soap bars), toothpastes, etc. in amounts such that the desired color is obtained using techniques known in the art. The pigments of this invention can also be added to other items which are desirable to be colored.

The following examples are intended to illustrate the invention and are not intended to limit the scope thereof. In the examples, all parts and percentages are by weight unless otherwise specified.

EXAMPLE 1

To 100 g of ice water is added 1 g of a poly-N-vinyl-5-ethyl-2-oxazolidinone (weight average molecular weight of about 15,000, prepared as taught in U.S. Pat. No. 3,539,540). To this is added a solution comprising 0.2 g of FD&C Blue No. 1 dye and 50 ml of ice water. The solution is gently stirred and the temperature is permitted to rise to room temperature. The resulting blue precipitate is filtered, rinsed and dried. No dye bleeding is observed when he precipitate is contacted with water at temperatures above 3° C.

EXAMPLE 2

A polyvinyl benzyl 5-methyl-2-oxazolidinone resin bead complexed with dye is prepared as follows. A mixture of 0.2 g of FD&C Yellow No. 10 and 0.5 g of FD&C Blue No. 1 are mixed with 100 g of water. To the dye solution is added 1 g of the aforementioned resin. The mixture is stirred at room temperature for 15 minutes. The beads are rinsed with water and dried. The beads exhibit a green color.

Several of the green beads are pressed into a bar of white soap and plced into an oven at 55° C. After 24 hours, no dye is observed to have migrated from the pigment into the soap.

EXAMPLE 3

To a citrate bottle is added 14 g of a 1 percent solution of polyvinyl alcohol, 126 g of distilled water, 0.1 g of FD&C Yellow No. 10, and 0.1 g of FD&C Blue No. 1. To the citrate bottle is next added 60 g of N-vinyl-5-ethyl-2-oxazolidinone and 0.6 g of $\alpha, \alpha'$,-azobis-(isobutyronitrile). The bottle is purged with nitrogen, capped with a cap lined with Saran brand film, placed into a canvas bag and placed into citrate bottle polymerizer. The bath is heated to 80° C. for 2 hours. The batch is cooled to 20° C. and the contents filtered through a 200 mesh screen. The yellow-green beads which are the polymer-dye pigment are water washed and air dried.

What is claimed is:

1. A method for preparing a substantially insoluble organic pigment wherein a water-soluble organic dye is contacted with a polymer comprising X-alkyl-2-oxazolidinone moieties in an aqueous medium under conditions such that the dye can become chemically bound to the polymer, and under conditions in which the polymer is at least partially soluble, and precipitating the resulting pigment to yield pigment particles having the insolubility characteristics of the polymer and the color characteristics of the dye under conditions at which the pigment is used.

2. A method of claim 1 wherein said polymer is a poly-N-vinyl-X-alkyl-2-oxazolidinone.

3. A method of claim 2 wherein said polymer is poly-N-vinyl-5-methyl-2-oxazolidinone or poly-N-vinyl-5-ethyl-2-oxazolidinone.

4. A method for preparing a substantially insoluble organic pigment wherein water-soluble dye is contacted with a polyvinylbenzyl-X-alkyl-2-oxazolidinone polymer to yield pigment particles having the insolubility characteristics of the polymer and the color characteristics of the dye.

5. A method of claim 4 wherein said polymer is polyvinylbenzyl-5-methyl-2-oxazolidinone.

6. A method of claim 1 wherein said polymer is a copolymer of a hydrophobic monomer and an N-vinyl-X-alkyl-2-oxazolidinone.

7. A method of claim 1 wherein said dye is selected from a member of the group consisting of FD&C Blue No. 1, FD&C Blue No. 2, FD&C Green No. 3, FD&C Green No. 6, FD&C Red No. 3, FD&C Yellow No. 5, FD&C Yellow No. 6, FD&C Yellow No. 7, and FD&C Yellow No. 10.

8. A method for introducing water-soluble organic dyes to toiletries such that the dyes added thereto are rendered substantially water-insoluble through the preparation of a polymer-dye pigment via the method of claim 1 and contacting said pigment with said toiletry in an amount sufficient to color said toiletry.

9. A pigment which is prepared via the method of claim 1.

10. A pigment which is prepared via the method of claim 2.

11. A pigment which is prepared via the method of claim 4.

12. A pigment which is prepared via the method of claim 6.

13. A pigment of claim 9 having a particle size from about 1 $\mu$m to about 5 $\mu$m.

14. A bar of soap containing a pigment which pigment is a substantially insoluble organic pigment, and wherein said pigment is prepared by contacting a water-soluble dye with a polymer comprising X-alkyl-2-oxazolidinone moieties to yield pigment particles having the insolubility characteristics of the polymer and the color characteristics of the dye.

15. A method for preparing a substantially insoluble organic pigment, said method comprising contacting a water-soluble dye in a reaction medium with N-vinyl-X-alkyl-2-oxazolidinone monomers and polymerizing said monomers to yield pigment particles having the insolubility characteristics of the polymer and the color characteristics of the dye.

16. A method for introducing water-soluble organic dyes to toiletries such that the dyes added thereto are rendered substantially water-insoluble through the preparation of a polymer-dye pigment via the method of claim 15 and contacting said pigment with said toiletry in an amount sufficient to color said toiletry.

17. A method of claim 1 wherein said dye is contacted with said polymer in an aqueous liquid at a low temperature at which the polymer is at least partially soluble and the temperature is raised in order to precipitate the polymer and yield said pigment particles.

18. A method of claim 17 wherein said polymer is poly-N-vinyl-5-methyl-2-oxazolidinone or poly-N-vinyl-5-ethyl-2-oxazolidinone and said low temperature at which the polymer is at least partially soluble is below about 3° C.

19. A pigment which is prepared via the method of claim 15.

20. A bar of soap containing the pigment of claim 19.

* * * * *